United States Patent
Schouten et al.

(10) Patent No.: US 10,435,799 B2
(45) Date of Patent: *Oct. 8, 2019

(54) PROCESS FOR THE PURIFICATION OF A CARBOXYLIC ACID-CONTAINING COMPOSITION

(71) Applicant: Avantium Knowledge Centre B.V., Amsterdam (NL)

(72) Inventors: Klaas Jan Pieter Schouten, Amsterdam (NL); Jan Cornelis Van Der Waal, Amsterdam (NL); Maria Varini, Amsterdam (NL); Gerardus Johannes Maria Gruter, Amsterdam (NL)

(73) Assignee: Avantium Knowledge Centre B.V., Amsterdam (NL)

( * ) Notice: Subject to any disclaimer, the term of this patent is extended or adjusted under 35 U.S.C. 154(b) by 0 days.

This patent is subject to a terminal disclaimer.

(21) Appl. No.: 15/575,789

(22) PCT Filed: May 20, 2016

(86) PCT No.: PCT/NL2016/050363
§ 371 (c)(1),
(2) Date: Nov. 20, 2017

(87) PCT Pub. No.: WO2016/186505
PCT Pub. Date: Nov. 24, 2016

(65) Prior Publication Data
US 2018/0142363 A1    May 24, 2018

(30) Foreign Application Priority Data
May 21, 2015  (NL) .................................. 2014842

(51) Int. Cl.
| | | |
|---|---|---|
| C25B 3/00 | (2006.01) | |
| C25B 3/02 | (2006.01) | |
| C07B 63/02 | (2006.01) | |
| C07D 307/68 | (2006.01) | |
| C07C 51/487 | (2006.01) | |
| C25B 11/12 | (2006.01) | |

(52) U.S. Cl.
CPC .............. C25B 3/02 (2013.01); C07B 63/02 (2013.01); C07C 51/487 (2013.01); C07D 307/68 (2013.01); C25B 11/12 (2013.01)

(58) Field of Classification Search
CPC ..................................................... C25B 3/02
USPC ................................................ 205/440, 442
See application file for complete search history.

(56) References Cited

U.S. PATENT DOCUMENTS

| | | |
|---|---|---|
| 3,819,503 A | 6/1974 | Casson et al. |
| 3,862,218 A | 1/1975 | Stautzenberger |
| 3,996,271 A | 12/1976 | Yokota et al. |
| 5,698,734 A | 12/1997 | Turner et al. |
| 5,763,648 A * | 6/1998 | Hashizume ................ B01J 8/22 562/414 |
| 8,242,292 B2 | 8/2012 | Yutaka et al. |
| 8,658,810 B2 | 2/2014 | Partin et al. |
| 8,791,278 B2 | 7/2014 | Shaikh et al. |
| 2011/0092720 A1 | 4/2011 | Yutaka et al. |
| 2013/0118910 A1* | 5/2013 | Teamey .................... C25B 1/00 205/427 |
| 2013/0172611 A1 | 7/2013 | Bhattacharyya |
| 2013/0345452 A1 | 12/2013 | Janka et al. |
| 2016/0201204 A1 | 7/2016 | Choi et al. |
| 2018/0142362 A1* | 5/2018 | Schouten ................ C07C 51/43 |

FOREIGN PATENT DOCUMENTS

| | | |
|---|---|---|
| PL | 161831 B2 | 8/1993 |
| WO | 199324440 A1 | 12/1993 |
| WO | 2011043660 A2 | 4/2011 |
| WO | 2011043661 A1 | 4/2011 |
| WO | 2015030590 A1 | 3/2015 |
| WO | 2016112091 A1 | 7/2016 |

OTHER PUBLICATIONS

Van Effen et al., "A Study of Aldehyde Oxidation at Glassy Carbon, Mercury, Copper, Silver, Gold and Nickel Anodes," J. Electroanal. Chem. (1979), vol. 103, pp. 383-397. (Year: 1979).*
Grabowski et al., "The Electrochemical Oxidation of 5-Hyrdoxymethylfurfural with the Nickel Oxide/Hydroxide Electrode," Electrochimica Acta (© 1991), vol. 36, No. 13, pp. 1995. (Year: 1991).*
Grabowski, Grzegorz, et al; "The Electrochemical Oxidation of 5-Hydroxymethylfurfural with the Nickel Oxide/Hydroxide Electrode;" Electrochimica Acta, vol. 36, No. 13, p. 1995; Printed in Great Britain in revised form on Jan. 31, 1991.
P. Parpot, et al; "Electrochemical Investigations of the Oxidation-Reduction of Furfural in Aqueous Medium Application to Electrosynthesis;" Electrochimica Acta, vol. 49 (2004), pp. 397-403; www.sciencedirect.com; May 6, 2003.
PCT Search Report and Written Opinion; PCT/NL16/50363 filed on May 20, 2016, Published as WO 2016/186505 on Nov. 24, 2016; 11 pages.
Cha, Hyun Gil et al., "Combined biomass valorization and hydrogen production in a photoelectrochemical cell", Nature Chemistry, Mar. 9, 2015, pp. 1-6, Macmillian Publishers Limited.

(Continued)

Primary Examiner — Edna Wong
(74) Attorney, Agent, or Firm — Suiter Swantz pc llo

(57) ABSTRACT

A carboxylic acid-containing composition, which composition contains an aldehyde, is purified in a process, which process comprises introducing the carboxylic acid-containing composition and an aqueous electrolyte into an electrolytic cell comprising electrodes; electrochemically oxidizing the aldehyde in the electrolytic cell to obtain an electrochemically oxidized product composition comprising a carboxylic acid derived from the aldehyde; and, optionally, separating carboxylic acid from the electrochemically oxidized product composition.

13 Claims, No Drawings

(56) References Cited

OTHER PUBLICATIONS

Chadderdon, David J. et al., "Electrocatalytic oxidation of 5-hydroxymethylfurfural to 2,5-furandicarboxylic acid on supported Au and Pd bimetallic nanoparticles", Green Chemistry, Apr. 24, 2014, pp. 3778-3786, vol. 16, The Royal Society of Chemistry.
Grabowski, Grzegorz et al., "The Electrochemical Oxidation of 5-Hydroxymethylfurfural with the Nickel Oxide/Hydroxide Electrode", Electrochimica Acta (1995), vol. 36, No. 13, p. 1995 (1995, 1991).
Parpot, P. et al., "Electrochemical investigations of the oxidation-reduction of furfural in aqueous medium Application to electrosynthesis", Electrochimica Acta, vol. 49 (2004), pp. 397-403; www.sciencedirect.com; May 6, 2003.
Tomas, Rogerio A. F. et al., "p-xylene Oxidation to Terephthalic Acid: A Literature Review Oriented toward Process Optimization and Development", Chemical Reviews, Jun. 14, 2013, pp. 7421-7469, vol. 113, No. 10, ACS Publications, American Chemical Society.
Van Effen, Richard M. et al., "A Study of Aldehyde Oxidation at Glassy Carbon, Mercury, Copper, Silver, Gold an Nickel, Anodes", J. Electroanal. Chem. (1979), vol. 103, pp. 383-397, 1979.
Vuyyuru, Koteswara Rao et al., "Oxidation of biomass derived 5-hydroxymethylfurfural using he4terogeneous and electrochemical catalysis", Catalysis Today, Jun. 8, 2012, pp. 144-154, vol. 195, Elsevier B. V.
International Search Report and Written Opinion dated Apr. 11, 2016 for PCT/NL2016/050362.

* cited by examiner

PROCESS FOR THE PURIFICATION OF A CARBOXYLIC ACID-CONTAINING COMPOSITION

The present invention relates to a process for the purification of a carboxylic acid-containing composition that further contains an aldehyde.

Carboxylic acids are prepared in a variety of methods. One suitable method is the oxidation of alcohols, ethers or aldehydes to the corresponding carboxylic acid. It has been found that the products of such oxidations may comprise several by-products. Such by-products may include partially oxidized intermediate products and even starting materials. One such by-product may be an aldehyde.

In several oxidations, there have been significant problems in purifying such oxidation products. When such oxidation products are obtained in a solvated form in a solvent, it has appeared that crystallization of such oxidation products from the solvent does not result in a pure crystallized carboxylic acid. Instead a so-called solid solution is obtained. In such case the impurity is present in the remaining mother liquor as well as in the solid solution.

An example of such a solid solution and the corresponding mother liquor is obtained in the preparation of terephthalic acid from p-xylene. This preparation results in a product comprising a mixture of terephthalic acid and 4-carboxybenzaldehyde (4-CBA). Another example is the preparation of furandicarboxylic acid from 5-substituted furfural, which yields a mixture of 2,5-furandicarboxylic acid (FDCA) and 5-formyl-furan-2-carboxylic acid (FFCA). The problem of the purification of terephthalic acid compositions is shown in e.g. U.S. Pat. No. 3,862,218, wherein improved crystallization is attempted by subjecting a composition comprising terephthalic acid and carboxyl-benzaldehyde to a thermal treatment. In more recent studies alternatives for such treatments are investigated, e.g. reduction of impurities by hydrogenation (cf. U.S. Pat. No. 5,698,734).

The difficulty of purifying FDCA compositions that comprise FFCA is exemplified in WO 2015/030590, wherein it is disclosed that the purification of FDCA-containing compositions that also contain FFCA are difficult to purify by re-crystallization. Therefore, it is proposed to use esterification and subsequent separation of the ester composition thus obtained.

It is evident that these proposed methods are cumbersome in that several different chemical compounds are formed that require separation. Therefore there is a need for a more simple method that does not involve the preparation of different impurities. It has been found that electrochemical oxidation of aldehydes provides such a simple purification method.

Accordingly, the present invention provides a process for the purification of a carboxylic acid-containing composition, which composition further contains an aldehyde, which process comprises
introducing the carboxylic acid-containing composition and an aqueous electrolyte into an electrolytic cell comprising electrodes,
electrochemically oxidizing the aldehyde in the electrolytic cell to obtain an electrochemically oxidized product composition comprising a carboxylic acid derived from the aldehyde; and, optionally,
separating carboxylic acid from the electrochemically oxidized product composition.

In the process according to the present invention the aldehyde is converted into a carboxylic acid. The process can very conveniently be used to remove aldehydes. In the flavor and fragrance industry the presence of aldehydes is often undesirable in view of an unpleasant taste or smell. The present invention is then very convenient. Also when complex biochemical compounds or biochemically active compounds, such as steroids, oxygenated flavors and fragrances, contain an undesired aldehyde moiety, such moiety can easily be converted by means of the present invention. When the carboxylic acid derived from the aldehyde is the same as the carboxylic acid that is present in the carboxylic acid-containing composition, no extraneous chemical compound is introduced into the process, so that the recovery of purified carboxylic acid is facilitated. Since the process of the present invention is of particular use in cases where these carboxylic acids are the same, the present invention particularly relates to processes wherein the aldehyde has the chemical formula R—CHO, wherein R represents an organic moiety and the carboxylic acid has the formula R—COOH, indicating that the aldehyde functionality and the carboxylic acid functionality are attached to the same organic moiety.

As indicated above, the compositions that can suitably be used as starting material for the process of the present invention can be obtained by the oxidation of organic compounds comprising alkyl, hydroxyl, alkoxy or formyl substituents. Therefore the process is preferably applied when the carboxylic acid-containing composition has been obtained from the oxidation of R—$R^1$, wherein R has the meaning as defined above and $R^1$ is selected from methyl, hydroxymethyl, alkoxymethyl, carbonyloxymethyl and formyl. When $R^1$ represents carbonyloxymethyl, the substituent is suitably an alkylcarbonyloxymethyl group, in which the alkyl group contains 1 to 4 carbon atoms. Suitable substituents are acetoxymethyl and propionoxymethyl. When $R^1$ is an alkoxymethyl group, the alkyl moiety preferably has from 1 to 6 carbon atoms.

The organic moiety R may be selected from any organic moiety. It therefore includes aliphatic, cycloaliphatic and aromatic groups. The aliphatic group may be selected from $C_1$-$C_6$-alkyl, such as methyl, ethyl, propyl, butyl, groups. Cycloaliphatic groups include in particular cyclohexyl groups. The aromatic groups may include phenyl, but also heteroaromatic groups. Also polyaromatic compound and polyheteroaromatic compounds may be used. R—$R^1$ can thus also comprise a mono- or polycyclic hydrocarbon aromatic compound, such as benzene, naphthalene, anthracene or phenanthrene, but also an oxygen- or nitrogen- or sulfur-containing heteroaromatic compound, such as furan, benzofuran, dibenzofuran, pyridine, quinoline, isoquinoline, or thiophene.

R may also contain one or more substituents. If desired, such substituents may include moieties that are also oxidizable under the electrochemical conditions of the present invention. Preferably, any substituent to R is inert under the electrochemical conditions of the present invention. Thus such substituents, if any, include halogen atoms, nitro groups, aromatic groups, such as phenyl groups, cycloaliphatic groups, such as cyclohexyl groups, alkyl groups, e.g. having from 2 to 6 carbon atoms, and carboxyl groups.

A significant advantage of the present invention resides in that a conventional oxidation tends to have a relatively low selectivity at high conversion. When the oxidation is brought to substantial completion, the selectivity of the eventual product may be relatively high, but the yield of this product is rather low since part of the starting material and product may have been converted to further oxidation products such as carbon monoxide and carbon dioxide. It is known that at increasing temperature and increased residence time the conversion of starting material ends up in a loss of product. This is e.g. known from R. A. F. Tomas et al., Chem. Rev., 113 (2013) pp 7421-7469, wherein it is stated that alter oxidation to the diaromatic carboxylic acid decarboxylation may occur at further oxidation. Such decarboxylation does not only occur in the aromatic acids, but also in the solvent when this is a carboxylic acid, such as acetic acid. The present invention allows a relatively low conversion to the eventual product.

As indicated above, it is particularly difficult to purify carboxylic acid-containing compositions when the carboxylic acid is an aromatic acid, in particular terephthalic acid or furandicarboxylic acid. Therefore, the present invention is particularly useful for the carboxylic acid-containing compositions wherein the carboxylic acid has the formula HOOC—$Ar^1$—COOH and the aldehyde has the formula OHC—$Ar^1$—COOH, wherein $Ar^1$ represents an arylene or heteroarylene moiety. Preferably, $Ar^1$ is selected from phenylene, furylene and pyridylene moieties.

When the carboxylic acid-containing composition has been obtained from the oxidation of a compound R—$R^1$, such oxidation may be carried out in a variety of ways. Such oxidation may e.g. be accomplished by potassium permanganate, but also by oxygen over an oxidation catalyst. Such catalysts include a silver oxide/copper oxide catalyst, a palladium or a palladium-platinum catalyst. Preferably, the oxidation of R—$R^1$ has been carried out by an oxygen-containing gas in the presence of a catalyst comprising cobalt, manganese and optionally bromine. Such an oxidation has suitably been conducted in a solvent comprising an aliphatic carboxylic acid or an aliphatic carboxylic anhydride. A particularly suitable solvent is acetic acid.

The carboxylic acid-containing composition of the process of the present invention comprises an aldehyde. The feedstock may comprise other components. Suitable alternative components include other intermediate compounds in the oxidation of R—$R^1$ organic compounds. Hence when R—$R^1$ is oxidized, such by products may be compounds wherein $R^1$ is a hydroxymethyl or formyl group. When the aldehyde has the formula OHC—$Ar^1$—COOH and $Ar^1$ is phenylene, alternative compounds may include xylene, e.g. p-xylene, substituted benzyl alcohol compounds or diformylbenzene. When $Ar^1$ is furylene, alternative components in the feedstock may include 5-hydroxymethylfurfural (HMF), diformyl-furan or hydroxymethyl-furancarboxylic acid. Additionally, esters of the aldehyde with the formula OHC—$Ar^1$—COOH may be present. The ester compound may also be the monoester or the diester of the aromatic dicarboxylic acid with formula HOOC—$Ar^1$—COOH, preferably the monoester so that the polarity and thus solubility of the compound in the aqueous electrolyte is significant. The alcohol component of the esters is suitably provided by a lower alkyl group, i.e. an alkyl group with 1 to 4 carbon atoms. Preferably, the carboxylic acid-containing composition comprises the carboxylic acid and the aldehyde in an amount of at least 90% wt, preferably, at least 95% wt, based on the weight of the carboxylic acid-containing composition.

In the carboxylic acid-containing composition the relative amounts of the carboxylic acid and aldehyde may vary within wide ranges, e.g. from 1000:1 to 90:10, preferably from 100:1 to 95:5, based on a weight by weight ratio. The present process is especially suited for a post-oxidation reaction of an intermediate product when a compound, e.g. HMF, an ether or ester thereof, or p-xylene, is oxidized in a different way in a first oxidation step. It has been known for a long time to oxidize xylene to terephthalic acid with an oxygen-containing gas using a catalyst system comprising cobalt, manganese and bromine (cf. U.S. Pat. No. 3,996,271). Also the oxidation of HMF or the ethers or esters of HMF with a similar catalyst system is known and has been described in WO 2011043660 and WO 2011043661. These oxidation reactions tend to lead to incomplete conversions. In order to increase the yield of the desired dicarboxylic acid the reaction mixture may be subjected to oxidation in a number of oxidation zones. Such a sequence of oxidation zones has been described in U.S. Pat. No. 8,791,278. In the process according to U.S. Pat. No. 8,791,278 HMF or an ether or ester thereof is oxidized in the presence of a Co, Mn and Br-containing catalyst in a primary oxidation zone so that an FDCA-containing product is obtained. The product contains other intermediate products. Therefore, the FDCA-containing product is separated into a mother liquor and a slurry stream, and the slurry stream is subjected to further oxidation in a secondary oxidation zone. The secondary oxidation zone operates at a higher temperature than the primary oxidation zone. In an alternative embodiment the product of the primary oxidation zone is without further separation passed into the secondary oxidation zone. In both embodiments this sequence entails that the feedstock for the secondary oxidation zone is to be heated further. This requires a significant additional energy input. Moreover, the experimental data in U.S. Pat. No. 8,791,278 show that the process described therein still yield noticeable amounts of FFCA. A drawback of the presence of FFCA or 4-carboxybenzaldehyde (4-CBA) resides in the fact that these impurities are extremely difficult to separate by crystallization from the desired product, i.e. 2,5-furan dicarboxylic acid or terephthalic acid, respectively. This is shown in e.g. U.S. Pat. No. 8,658,810 describing a purification process of crude FDCA by esterification and subsequent separation of the various esters, and U.S. Pat. No. 8,748,479 describing a process wherein crude FDCA is hydrogenated and the hydrogenation products are separated.

When the process according to the present invention is applied to the product of the catalytic oxidation of xylene, dimethylfuran, HMF or an ester or ether thereof, intermediate products such as 4-carboxybenzaldehyde (4-CBA) or FFCA can easily be further oxidized to terephthalic acid and FDCA. The process according to the present invention is thus advantageously used as a purification step for the product that is obtained in a conventional oxidation of aromatic starting materials such as xylene, dimethylfuran, HMF or an ester or ether thereof. The present process then provides a simple economic method to complete conversion of the intermediates that tend to be difficult to separate.

Whereas the application of a sequence of oxidation zones tends to be cumbersome in that further heating is required and still no complete conversion can be obtained easily, the present process allows for the electrochemical oxidation at mild conditions whereas complete oxidation of the aldehyde of formula OHC—$Ar^1$—COOH can be obtained. Since the electrochemical oxidation according to the present invention readily leads the conversion to completion, there is no necessity to maximize the yield in the conventional oxidation. When the oxidation product contains up to 10% wt of the aldehyde compound, such an amount can still easily be converted into the desired carboxylic acid.

After the oxidation of R—$R^1$ the resulting oxidized product is typically subjected to some form of purification before the thus purified product is used as feedstock for the process according to the present invention. During the purification, catalyst components, e.g. cobalt, manganese and/or bromine compounds, are removed from the oxidation product, e.g. by washing. It is known that during the oxidation of the compound R—R$^1$ also by-products are formed that cause coloration. In US 2013/0345452 it has been made the objective of the process described therein to reduce the amount of colorants, also known as color bodies, in the preparation of FDCA from HMF or an ether or ester thereof over a catalyst containing cobalt, manganese and bromine. In conventional processes these colorants have to be removed by one or more re-crystallizations. In the process according to US 2013/0345452 the colorants are removed by means of hydrogenation of crude FDCA. Surprisingly, it has now been found that during the oxidation of the OHC—Ar$^1$—COOH feedstock of the present invention in the electrolytic cell also colorants are removed. The process according to the present invention therefore not only increases the yield of the desired dicarboxylic acid by converting the aldehyde into the desired dicarboxylic acid, but it also reduces the content of colorants, which facilitates the isolation of colorless product from the resulting product in the electrolytic cell. This constitutes a significant additional advantage of the present process.

The skilled person will know what components are required to form an electrolytic cell. The cell comprises an anode, a cathode and an electrolyte. The anode and cathode are connected to a power supply, capable of applying a potential over the anode and cathode. The electrolytic cell may further be provided with a reference electrode. The reference electrode may be a standard hydrogen electrode and provides an indication for the potential to cause the oxidation reaction. Typically the electrolytic cell is operated in the absence of a reference electrode.

The electrolytic cell may be a divided cell or an undivided cell. In a divided cell a separation has been established between the electrolyte that is in contact with the anode and the electrolyte that is in contact with the cathode. Such a separation may be achieved by a semi-porous membrane, made from e.g. sintered glass, porous porcelain, polytetrafluoro ethylene (PTFE or Teflon®) or polyolefin such as polyethylene or polypropylene. In an undivided cell the aqueous electrolyte and the feedstock are in contact with both the anode and the cathode. Such an undivided cell is easier to operate than a divided cell; thus that represents an advantage. Operation in an undivided cell enables not only the oxidation of the aromatic aldehyde compound of formula (1), but it also makes it possible that undesired reactions take place at the cathode, e.g. the reductive coupling of aldehydes to a diol. Since such reactions do not take place when a divided cell is being used, the application of a divided cell is especially preferred.

The electrodes may be made of a variety of materials. Such materials include the noble metals, such as gold, silver, and the metals of the platinum group and carbon. Very good results have been obtained with electrodes comprising non-noble metals, i.e. all metals other than those mentioned above. In accordance with a preferred embodiment of the present invention at least one of the electrodes comprises a non-noble metal, and/or a hydroxide and/or oxide thereof. As indicated above, in this specification the noble metals are selected from ruthenium, rhodium, palladium, silver, osmium, iridium, platinum, and gold. The non-noble metals are all those metals other than these noble metals. The non-noble metals suitably include the base metals, lead, iron, copper, tin, nickel and compounds or alloys thereof. A suitable alloy of iron is e.g. stainless steel, comprising i.a. a significant amount of chromium. The electrolytic cell may contain an anode and a cathode that both contain a non-noble metal. However, the non-noble metal does not need to be the same in both the anode and the cathode. Another very suitable material for application as electrode is carbon, in particular graphite. The cathode material is suitably carbon. The electrode comprises the non-noble metal does not need to contain the metal in its elemental form. The electrode may suitably comprise noble metal with the oxide and/or hydroxide thereof. Such an electrode may be similar to the one used in the article by Grabowski et al. (Electrochimica Acta, 36 (1991) 1995). It has been found that the use of nickel or copper as material for the electrodes is advantageous. Accordingly, the electrolytic cell has preferably been provided with at least one electrode that comprises a non-noble metal, its oxide and/or its hydroxide, which non-noble metal is nickel or copper. When reference is made to a non-noble metal-containing electrode this indicates that the electrode in question may comprise the non-noble metal in elemental form, as its oxide and/or as its hydroxide. The non-noble metal-containing, e.g. nickel, electrode can be in the form of a rod. However, in order to enhance the surface of the electrode, the non-noble metal-containing, e.g. nickel, electrode is suitably in the form of a plate, a mesh, a metal foam or in the form of small particles on a carrier, such as a carbon carrier. The non-noble metal can be used as the material for either of the anode or the cathode, preferably for the anode. As indicated above, carbon is suitably used as material for the cathode. Carbon may also be used as substrate for an electrode onto which metal has been impregnated.

The electrolytic cell contains an aqueous electrolyte. In order to facilitate the solubility of the carboxylic acid in the electrolyte, the aqueous electrolyte suitably is an alkaline solution. The alkalinity facilitates the dissolution of the carboxylic acid, both as the starting material and as the product. The alkalinity may also enhance the solubility of the aldehyde when it has the formula OHC—Ar$^1$—COOH. Suitably, the alkaline solution comprises an alkaline compound selected from an alkali metal hydroxide, alkali metal carbonate, alkali metal bicarbonate, ammonia, ammonium carbonate, ammonium bicarbonate, a trialkylamine and combinations thereof. The use of weak acids and bases, such as carbonate and bicarbonate, has the advantage that they provide a buffering effect. The trialkylamine suitably contains alkyl groups with 1 to 4 carbon atoms, preferably 1 or 2 carbon atoms. Suitable amines include trimethyl amine and triethyl amine. The use of organic amines is advantageous since these compounds can be relatively easily recovered from the aqueous electrolyte after the electrochemical oxidation. Suitable recovery methods include extractive distillation.

The aqueous electrolyte may comprise such an amount of an alkaline compound that the aqueous electrolyte, in spite of the presence of the carboxylic acid that is produced and/or that is present in the carboxylic acid-containing composition is still alkaline. The pH of the aqueous electrolyte is then suitably in the range of 7.5 to 13. When the pH is sufficiently high, the formation of additional carboxylic acid by the oxidation of the aldehyde does not render the electrolyte neutral or acidic. To the electrolyte a buffer solution may have been added. Such an addition, however, is not required. As the carboxylic acid being a weak acid is present in the carboxylic acid-containing composition, the electrolyte is already buffered.

The aqueous electrolyte does not need to be alkaline. It is feasible to employ a mixture of the carboxylic acid-containing composition in water to which no base has been added. The electrolyte may then be formed by the combination of water and carboxylic acid-containing composition, and the ions are provided by the carboxyl function in the carboxylic acid and optionally by the aldehyde of formula OHC—$Ar^1$—COOH, if such an aldehyde is used in the present process. Thus, the pH of the aqueous electrolyte may be acidic, e.g. having a value of 0.5 to 7.0. A drawback of using water without the addition of a base resides in the reduced solubility of the carboxylic acid-containing composition as well as a lower conductivity of the electrolyte.

Therefore, the aqueous electrolyte suitably contains such an amount of alkaline compound that the solubility of the carboxylic acid and the conductivity of the electrolyte are satisfactory, whilst the amount of alkaline compound is lower than the equivalent amount of carboxyl groups in the carboxylic acid-containing composition. The pH of such solutions may then vary from e.g. 1.0 to 7.5. The amount of alkaline compound may thus be selected within wide ranges. Preferably, the amount is in the range of 0.1 to 3.0 equivalents per equivalent carboxyl group in the carboxylic acid-containing composition, more preferably from 0.5 to 1.5 equivalents per equivalent carboxyl group.

The electrolyte does not need to consist of water and ions only. The electrolyte may conveniently also comprise one or more organic diluents. Suitable diluents are water-miscible organic compounds, such as alcohols, aldehydes, ketones or sulfoxides. Suitable diluents include one or more of methanol, ethanol, n-propanol, i-propanol, n-butanol, i-butanol and t-butanol, formaldehyde, acetone and dimethylsulfoxide. The electrolyte suitably contains water at least in an amount of 5% wt, based on the weight of the electrolyte, more preferably at least 50% wt, and most preferably at least 90% wt, based on the weight of the electrolyte.

The conditions in the electrolytic cell can be determined by the person skilled in the art. It is evident that the potential and current in the electrolytic cell must be of a sufficient magnitude to produce the chemical reactions desired. These reactions include the conversion of the aldehyde functionality in the aldehyde into a carboxyl functionality on the anode and the reduction of water molecules to molecular hydrogen on the cathode. The potential difference between anode and cathode in the electrolytic cell is suitably below 10 V, more preferably below 1.23 V. By applying a voltage below 1.23 V the electrolysis of water is avoided. The desired voltage can be provided by installing a predetermined current or current density. The current may vary within wide limits as determined by the shape, size and other parameters of the electrolytic cell. Typically, the current density is varied between 0.1 mA/cm$^2$ and 10 A/cm$^2$, preferably from 0.2 mA/cm$^2$ to 1 A/cm$^2$. The total current is adapted according to the surface of the smallest electrode. The reaction is typically prolonged at these conditions until the desired reactions take place.

The oxidation of the aldehyde can be achieved at a wide range of reaction conditions. The temperature and pressure can be ambient. Obviously, the skilled person may apply elevated temperatures and pressures if he would so desire. For instance, if the carboxylic acid-containing composition becomes available at elevated temperature and pressure from a preceding oxidation of a compound R—$R^1$ these prevailing temperatures and pressures may be maintained in the electrolytic cell during the oxidation of the aldehyde. Accordingly, the aldehyde is suitably oxidized at a temperature in the range of 10 to 250° C. and at a pressure in the range of 0.5 to 20 bar. The use of elevated temperatures has the advantage that the solubilities of the aldehyde and of the carboxylic acid are increased. The residence time of the feedstock in the electrolytic cell is also selected such that a sufficient charge has been supplied to the anode to allow for a substantially complete conversion of the aldehyde functionality to the carboxyl functionality. Evidently, factors that influence residence time of the carboxylic acid-containing composition in the electrolytic cell include the concentration of the aldehyde in the electrolyte, the current and the potential, current density, the surface area of the electrodes, the degree of homogenization of the electrolyte and the volume of the electrolytic cell. Typically, the residence time of the carboxylic acid-containing composition in the electrolytic cell is in the range of 0.1 to 24 hrs.

The process according to the present invention can be carried out in a batch mode. In a batch mode the residence time may suitably be in the range of 0.25 to 24 hrs, preferably, from 1 to 8 hrs. Preferably, the process is conducted in a continuous mode. An example of a continuous electrolytic cell has been described in U.S. Pat. No. 3,819,503. Although the known continuous electrolytic cell has been described for the manufacture of oxyhalogen compounds, a similar cell can be used for the continuous oxidation of the aldehyde according to the present invention. In a continuous electrolytic cell the residence time may be shortened; suitably the residence time is then in the range of 0.1 to 10 hrs, preferably from 0.25 to 8 hrs.

After the oxidation of the aldehyde a reaction medium is obtained that comprises carboxylic acid and electrolyte. The electrolyte tends to be alkaline. Therefore, the carboxylic acid obtained after the electrochemical oxidation of the aldehyde is suitably recovered by acidizing the electrochemically oxidized product composition and allowing carboxylic acid to precipitate. As indicated above, most if not all of the colorants have been removed during the oxidation in the electrolytic cell. Therefore, the precipitated product is virtually colorless. If the solubility of the carboxylic acid is such that precipitation is difficult to achieve, alternative recovery methods may be considered, including evaporation of the aqueous electrolyte.

The invention will be further illustrated by means of the following examples.

EXAMPLE 1

In order to mimic a purification of a carboxylic acid-containing composition that is obtained by the oxidation of HMF a solution comprising FFCA and FDCA, each in a concentration of 50 mmoles per liter 0.5 M NaOH in water, was made. A divided electrolytic cell consisting of two compartments separated from each other by means of a porous glass frit, was used. The solution comprising FFCA and FDCA was placed in one compartment, i.e. the anode compartment, of the divided electrolytic cell. The anode compartment was further provided with an anode, i.e. a nickel plate. The other compartment, i.e. the cathode compartment, was provided with an aqueous solution of 0.5M NaOH and a cathode consisting of a nickel mesh. Both compartments were stirred. At room temperature, i.e. about 20° C., a current was applied on the electrodes. The current was 6.4 mA, corresponding with a current density of 0.8 mA/cm$^2$. The voltage measured at the anode was 0.4-0.7 V versus reference Ag/AgCl electrode. The current was continued for 6.7 hours. At the anode the FFCA was oxidized to FDCA. At the cathode hydrogen evolved. After 6.7 hours the content of the solution in the anode compartment was analyzed. The conversion of FFCA was measured as molar percentage of aldehydes that have disappeared. Apart from FFCA and FDCA, no other compounds were detected in the solution of the anode compartment. That means that the result of a Cannizarro reaction that may have taken place in the anode compartment forming 5-hydroxymethyl-furan-2-carboxylic acid (HMFCA) and FDCA was offset by the further oxidation of any HMFCA that is formed, at the anode to FDCA. Thereby the yield of FDCA is optimized. The aldehyde conversion is shown in Table 1 below.

To show the suitability of the present process for other aldehydes, another experiment was conducted with 50 mM/L furfural and 50 mM/L furoic acid in 0.5 M NaOH. The reaction with furfural and furoic acid lasted 6.7 hours. The conversion of the aldehyde is shown in Table 1.

TABLE 1

| Experiment No. | Reagent | Aldehyde conversion, % |
|---|---|---|
| 1 | FFCA + FDCA | 90.0 |
| 2 | Furfural + furoic acid | 71.9 |

The experiments show that the electrochemical oxidation of an aldehyde that is contained in a carboxylic acid-containing composition leads to conversion of the aldehyde into the corresponding acid in a major proportion without leading to undesired by-products.

EXAMPLE 2

A series of experiments were carried out in substantially the same way as described for the experiments in Example 1. The electrolyte was 0.5M NaOH solution. The feedstock and the amount thereof (in mmoles per liter NaOH solution) have been shown in Table 2. Table 2 also shows the reaction temperature as well as residence time of the feedstock in the electrolytic cell. The electrodes both consisted of nickel mesh. The current applied amounted to 22.4 mA, corresponding with a current density of 0.8 mA/cm$^2$ and a potential at the anode of 0.4-0.8 V versus a reference Ag/AgCl electrode. In Experiment No. 4 a feedstock was used that consisted of crude FDCA, obtained in the oxidation of methoxymethylfurfural with oxygen in acetic acid using a Co, Mn and Br-containing catalyst. The crude FDCA contained about 1% wt FFCA, based on the total crude FDCA, and minor amounts of color bodies. The Table also shows the conversion of the aldehyde.

TABLE 2

| Exp. No. | Feedstock | Reaction temperature, °C. | Residence time, hr | Aldehyde conversion, % |
|---|---|---|---|---|
| 3 | 5 mM FFCA + 45 mM FDCA | 20 | 1.7 | 100.0 |
| 4 | 50 mM crude FDCA | 20 | 1.0 | 100.0 |

The above results show the suitability of the present process in the purification of mixtures of FDCA and FFCA. Whereas the feedstock of experiment No. 4 shows a brown/yellow color, the product after electrochemical oxidation is almost colorless, indicating that major color bodies have been removed.

EXAMPLE 3

The use of an undivided electrolytic cell is also shown in Experiment Nos. 5-8. A glass vessel used as an undivided electrolytic cell was loaded with a solution of feedstock as indicated in Table 3 having a concentration of the number of millimoles indicated per liter aqueous 0.5 M NaOH, an anode and a cathode. The material of the anode was a nickel mesh as indicated in Example 2, and the cathode was made of nickel mesh or carbon paper. A current of 22.4 mA was applied between the anode and cathode. The electrochemical oxidation was conducted at room temperature, i.e. 20° C., for a period as shown as the residence time in Table 3. The feedstock, cathode material and aldehyde conversion in the aqueous electrolyte after the residence time indicated are also shown in Table 3. The electrolyte was also varied by using 0.5 M NaOH in water or 0.5 M triethylamine (TEA) in water. The feedstock in experiment Nos. 6-8 was crude FDCA, including 1% wt FFCA, based on the total crude FDCA and minor amounts of color bodies.

TABLE 3

| Exp. No. | Feedstock | Cathode material | Electrolyte | Residence time, hr | Aldehyde conversion, % |
|---|---|---|---|---|---|
| 5 | 50 mM FFCA + 50 mM FDCA | Ni mesh | NaOH | 5.6 | 97.9 |
| 6 | 150 mM crude FDCA | Ni mesh | NaOH | 5.6 | 98.4 |
| 7 | 50 mM crude FDCA | Carbon paper | NaOH | 3.5 | 100.0 |
| 8 | 50 mM crude FDCA | Carbon paper | TEA | 5.1 | 99.1 |

In addition to a virtually complete conversion of the aldehyde compound, the resulting product in experiment Nos. 5-8 also showed considerably less coloring, indicating that also color bodies were oxidized.

EXAMPLE 4

To show that the present process can also be applied to aldehydes other than FFCA, two further experiments were conducted on a feedstock comprising benzaldehyde and benzoic acid in one experiment and on 4-carboxybenzaldehyde (4-CBA) and terephthalic acid in the second experiment. The experiments were conducted in a way similar to the experiments in Example 2. The divided electrolytic cell was used. Both the anode and the cathode were nickel mesh electrodes. The electrolyte was 0.5M NaOH. The reaction temperature was 20° C. and the current was 22.4 mA. The electrochemical oxidation was continued for 5.6 hours.

The concentration of the materials (number of millimoles per liter) and the results are shown in Table 4.

TABLE 4

| Experiment No. | Feedstock | Aldehyde conversion, % |
|---|---|---|
| 9 | 5 mM benzaldehyde + 45 mM benzoic acid | 71.4 |
| 10 | 50 mM 4-CBA + 50 mM terephthalic acid | 81.6 |

The results show that also benzoic acid and terephthalic acid can conveniently be purified by applying the process according to the invention.

EXAMPLE 5

Five more experiments were performed in substantially the same way as described for the experiments in Example 1. The electrolyte was 0.5 M NaOH solution. The feedstock was a solution of 50 mM crude FDCA (containing 1% wt FFCA) per liter of 0.5 M aqueous NaOH. The anode was either a stainless steel plate (Exp. No. 11), a tin plate (Exp.

No. 12), a copper mesh (Exp. No. 13), carbon paper (Exp. No. 14) or a platinum mesh (Exp. No. 15). The cathode was a nickel mesh, as used in Exp. No. 2. The reaction temperature was 20° C. The current applied amounted to 22.4 mA.

The total conversion after 5.6 hours was recorded for Exp. Nos. 11, 14 and 15, whereas the total conversion of aldehyde for Exp. No. 12 was reached after 3.2 hours and for Exp. No. 18 already after 0.4 hours. The results are summarized in Table 5.

TABLE 5

| Exp. No. | Anode material | Residence time, hr | Aldehyde conversion, % |
|---|---|---|---|
| 11 | Stainless steel | 5.6 | 92.3 |
| 12 | Tin plate | 3.2 | 100 |
| 13 | Copper mesh | 0.4 | 100 |
| 14 | Carbon paper | 5.6 | 78.0 |
| 15 | Platinum mesh | 5.6 | 33.0 |

The results show that all electrodes enable the oxidation of the aldehyde, although non-noble metals that are used as anode material perform better than noble metals, even when the noble metal is present as anode with a larger surface area. The copper electrode is particularly effective. Also the carbon electrode is significantly more efficient than the platinum electrode.

COMPARATIVE EXPERIMENT

An acid product was obtained from the oxidation of 5-methoxymethylfurfural in acetic acid in the presence of a catalyst that contained cobalt, manganese and bromine. The acid product has precipitated and the solid product was filtered to remove acetic acid. Subsequently, the acid composition washed with water and the amount FFCA therein was determined. The product was subsequently taken up in water at 90° C. and completely dissolved. The weight ratio of acid product to water was about 1:150. The solution was allowed to cool to 20° C., and a precipitate was formed. The precipitate was filtered off and dried. This precipitate was recrystallized two more times, using the above procedure. The yield of solids obtained, based on the weight of the acid product, was determined. The amount of FFCA in the final precipitate was also determined. The results are shown in Table C1, below.

The recrystallization experiment was repeated with the same acid product as starting material, but the product was dissolved in acetic acid at 100° C. The weight ratio of acid product to acetic acid was about 1:150. The solution was allowed to cool to 5° C., and a precipitate was formed. The precipitate was filtered off and dried. The yield of solids obtained after three recrystallizations, based on the weight of the acid product, was determined. The amount of FFCA in the final precipitate was also determined. The results are shown in Table C1, below.

The recrystallization experiment was repeated with the same acid product as starting material, but in the product was dissolved in methanol at 60° C. The weight ratio of acid product to methanol was about 1:26. The solution was allowed to cool to −20° C., and a precipitate was formed. The precipitate was filtered off and dried. The yield of solids obtained after three recrystallizations, based on the weight of the acid product, was determined. The amount of FFCA in the final precipitate was also determined. The results are shown in Table C1 below.

TABLE C1

| Exp. No. | Solvent | FFCA (acid product), ppmw | FFCA (recrystallized), ppmw | Solids Yield, % wt |
|---|---|---|---|---|
| C1 | Water | 6244 | 3382 | 53 |
| C2 | Acetic acid | 6244 | 1894 | 60 |
| C3 | Methanol | 6244 | 486 | 15 |

These results show that recrystallization only has a modest effect on the removal of FFCA from the FDCA product whilst the loss of FDCA product is considerable.

The invention claimed is:

1. A method for the purification of a carboxylic acid-containing composition, which composition further contains an aldehyde, comprising:
   introducing the carboxylic acid-containing composition and an aqueous electrolyte into an electrolytic cell comprising electrodes; and
   electrochemically oxidizing the aldehyde in the electrolytic cell to obtain an electrochemically oxidized product composition comprising a carboxylic acid derived from the aldehyde,
   wherein the carboxylic acid has the formula HOOC—$Ar^1$—COOH and the aldehyde has the formula OHC—$Ar^1$—COOH, wherein $Ar^1$ represents an arylene or heteroarylene moiety.

2. The method according to claim 1, wherein $Ar^1$ is selected from phenylene, furylene and pyridylene moieties.

3. The method according to claim 1, wherein the electrolytic cell is a divided cell.

4. The method according to claim 1, wherein at least one of the electrodes comprises a non-noble metal and/or an oxide and/or a hydroxide thereof.

5. The method according to claim 1, wherein carbon is used as cathode material in the electrolytic cell.

6. The method according to claim 1, wherein the aqueous electrolyte comprises an alkaline solution.

7. The method according to claim 6, wherein the alkaline solution comprises an alkaline compound selected from an alkali metal hydroxide, alkali metal carbonate, alkali metal bicarbonate, ammonia, ammonium carbonate, ammonium bicarbonate, a trialkylamine and combinations thereof.

8. The method according to claim 1, wherein the potential difference between anode and cathode in the electrolytic cell is at most 10 V.

9. The method according to claim 1, wherein the aldehyde is oxidized at a temperature in the range of 10 to 250° C. and at a pressure in the range of 0.5 to 20 bar.

10. The method according to claim 1, wherein the residence time of the carboxylic acid-containing composition in the electrolytic cell is in the range of 0.1 to 24 hours.

11. The method according to claim 1, which method is conducted in a continuous mode.

12. The method according to claim 1, wherein the carboxylic acid derived from the aldehyde is recovered by acidizing the electrochemically oxidized product composition and allowing carboxylic acid to precipitate.

13. The method according to claim 1, further comprising separating the carboxylic acid derived from the aldehyde from the electrochemically oxidized product composition.

* * * * *